United States Patent [19]

Klopotek et al.

[11] 3,965,025

[45] June 22, 1976

[54] METHOD FOR MANUFACTURING ALKALINE DETERGENTS AND DESINFECTANTS

[75] Inventors: Alojzy Klopotek, Nowy Dwor Mazowiecki; Jan Profic, Warsaw; Jerzy Umiński, Nowy Dwor Mazowiecki; Gabriela Dziala, Legionowo, all of Poland

[73] Assignee: Instytut Chemii Przemysłowej, Warsaw, Poland

[22] Filed: Feb. 5, 1974

[21] Appl. No.: 439,758

[30] Foreign Application Priority Data

Feb. 7, 1973 Poland .................................. 160632
Feb. 14, 1973 Poland .................................. 160733

[52] U.S. Cl. ............................ 252/106; 423/299; 423/315; 424/221
[51] Int. Cl.² ...................... C11D 3/48; C01B 25/00
[58] Field of Search ........... 423/298, 300, 305, 315; 424/204, 205, 221; 252/106, 156

[56] References Cited

UNITED STATES PATENTS 2,977,315  3/1961  Scheib et al. ...................... 252/106
2,997,421  8/1961  Hosmer et al. ..................... 252/106

*Primary Examiner*—Oscar R. Vertiz
*Assistant Examiner*—Gregery A. Heller
*Attorney, Agent, or Firm*—Haseltine, Lake & Waters

[57] ABSTRACT

A method for manufacturing bromine-polyphosphate and bromine-iodine-polyphosphate complex compounds having detergent and disinfecting properties is described.

These compounds disinfectant a wide range of application as efficient disinfectants and disinfectants detergents in such fields as medicine, veterinary medicine, agriculture, dairy and meat industries.

7 Claims, No Drawings

METHOD FOR MANUFACTURING ALKALINE DETERGENTS AND DESINFECTANTS

This invention relates to a method for manufacturing alkaline detergents and disinfectants comprising bromine-polyphosphate and bromine-iodine polyphosphate complex compounds. Compounds prepared according to the present invention are characterized by their bactericidal action, particularly in relation to acid-resistant bacteria and to bacteria which produce spores and fatty areolas, as well as by their excellent detergency effects and resistance to hard water. These agents may be used in the treatment of diseases of the respiratory system, such as bronchopneumonia and lung tuberculosis. Other uses include washing and disinfecting in one operation used in apparatus and equipment in agriculture, food industry, veterinary medicine, medicine and municipal installations.

The aqueous solutions of these agents are alkaline in reaction.

The methods for manufacturing this class of alkaline complex compounds are not known. This hitherto used alkaline disinfectants contain active chlorine in the form of chlorinated lime, sodium hypochlorite and other alkaline compounds.

The main drawbacks of these hitherto used alkaline agents are their low efficiency, noxiousness to human beings and animals, a strong corroding action against the materials of equipment and installations being disinfected, the necessity of using separate agents for washing and for disinfecting, and as well the necessity of applying elevated temperatures (60 – 100° C).

There are indeed agents with bactericidal action comprising iodine and derivatives of phosphoric acid, e.g., as described in German Pat. No. 1,139,611, but they differ from those of the present invention by their acid reaction, use of other substrates and different method of manufacturing, as well as different chemical structure of the agent.

The scope of the invention includes a method for manufacturing efficient, stable, alkaline, disinfecting and washing complex compounds having no detrimental side effects.

The method for manufacturing the bromine and bromine-iodine complex compounds, according to a the present invention, having the general formulas:
$Me[PO_3Me]_x$-OH...Br-Br...HO-$[PO_3Me]_x$Me for the bromine compounds and
$Me[PO_3Me]_x$-OH...J-Br...HO-$[PO_3Me]_x$Me for the bromine-iodine compounds,
where Me represents atom of alkali metal and x is an integer from 2 to 50, comprises: a/ In the case of preparing bromine polyphosphate complex compounds: reacting a dibromo iodate of an alkali metal $[IBr_2]^-$, or a bromine non-ionic surfactant complex compound, with polyphosphates of alkali metals at a temperature in the range of 0°–50°C. The stoichiometric proportion of reactants is equal to not more than 1 mole dibromoiodate ion, $[IBr_2]^-$, or 1 mole of the bromine surfactant complex compound per 2 moles of polyphosphate. The dibromoiodate of an alkali metal, which is indispensable in this method, e.g. $KIBr_2$, may be prepared by reacting bromine with a saturated aqueous solution of an alkali iodide in stoichiometric or nearly stoichiometric proportions at a temperature in the range of 0°–60°C. The bromine-non-ionic surfactant complex compounds may be prepared by reacting the above mentioned alkali dibromoiodate with a non-ionic surfactant in a stoichiometric proportion of not more than 1 mole bromide per 1 mole of surfactant.

The reactions of synthesis according to the present invention conform to the following equations:

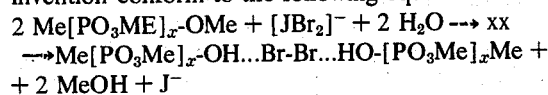

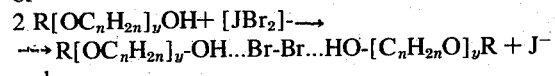

or

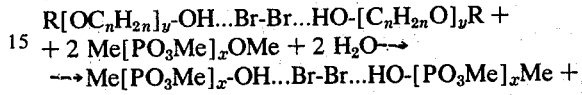

and
$R[OC_nH_{2n}]_y$-OH...Br-Br...HO-$[C_nH_{2n}O]_yR$ +
+ 2 $Me[PO_3Me]_x$OMe + 2 $H_2O$ →
→$Me[PO_3Me]_x$-OH...Br-Br...HO-$[PO_3Me]_x$Me +

+ 2 R $[OC_nH_{2n}]_{y\ y}$ -OH + 2 MeOH. b/ In the case of manufacturing bromine-iodine-polyphosphate complex compounds, the corresponding procedure comprises reacting iodine bromide or bromine-iodine-non-ionic surfactant complex compounds with alkali polyphosphates at a temperature in the range of 0°–50°C. The stoichiometric proportion of reactants is equal to not more than 1 mole of iodine bromide or 1 mole of the iodine-bromide-surfactant complex compound per 2 moles of polyphosphate.

The iodine bromide, which is indispensable in this method, may be prepared by reacting bromine with iodine in stoichiometric proportion at a temperature in the range of 0°–60°C. The iodine-bromide-non-ionic surfactant complex compounds are prepared by reacting the above mentioned iodine bromide, JBr, with non-ionic surfactants in a stoichiometric proportion of not more than 1 mole iodine bromide per 2 moles of surfactant.

The reaction sequence according to the present invention conforms to the following equations;

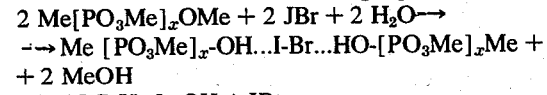

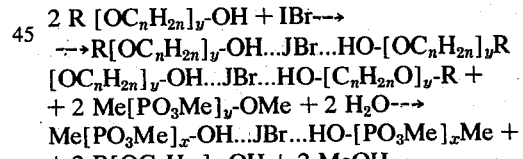

$[OC_nH_{2n}]_y$-OH...JBr...HO-$[C_nH_{2n}O]_y$-R +
+ 2 $Me[PO_3Me]_y$-OMe + 2 $H_2O$ →
$Me[PO_3Me]_x$-OH...JBr...HO-$[PO_3Me]_x$Me +
+ 2 $R[OC_nH_{2n}]_y$-OH + 2 MeOH.

The bromine-iodine-polyphosphate complex compounds according to the present invention are stabilized additionally with alkali bromides or alkaline earth bromides.

The method for manufacturing according to the present invention gives the bromine-polyphosphate or bromine-iodine-polyphosphate complex compounds which are characterized by their strong bactericidal action against acid-resistant bacteria, to bacteria which form spores and to bacteria possessing fatty areolas, as well as by their excellent washing action. The agents based on these compounds may be used in the prophylaxis and therapy of the diseases of the respiratory system, as well as in washing and disinfecting the apparatus and equipment in the food industry.

The following Examples illustrate the preparation of the compounds of the present invention.

EXAMPLE I

Preparation of the bromine-iodine complex compounds with polyphosphates

In a reactor fitted with a stirrer and cooling system a saturated aqueous solution of potassium iodide is prepared by mixing 2 kg potassium iodide with 1.4 kg water, and then 1.93 kg liquid bromine is introduced, with stirring, at a temperature in the range of 0° to 60°C. The aqueous solution of potassium dibromineiodide $KJBr_2$ obtained in this manner is then mixed with 8.9 kg sodium tripolyphosphate represented by formula $Na_5P_3O_{10}$ at a temperature not higher than 50° C. The product obtained in this manner is diluted, according to its use, for direct application with water in a weight proportion from 1:20 to 1:200.

EXAMPLE II

Preparation of the bromine-iodine complex compounds with polyphosphates

In a reactor fitted with stirrer and cooling system 2 kg crystalline iodine is mixed with 1.26 kg liquid bromine at a temperature of 50° C. The prepared iodine bromide is then mixed with 16.74 kg oxyethylenized octadecyl alcohol corresponding to the formula $C_{18}H_{37}$-$(OC_2H_4)_{18}$-$OH$ and containing only small amounts of water, with simultaneous cooling of the reaction mixture, so at to have the temperature of the reaction mixture below 60° C. This liquid reaction mixture is then mixed with 5.8 kg sodium polyphosphate corresponding to the formula $Na_5P_3O_{10}$ at a temperature not higher than 50° C and 0.6 kg sodium bromide is added, to stabilize the product.

The preparation thus obtained is diluted, according to its use, with water for direct application with water in a weight proportion from 1:20 to 1:200.

EXAMPLE III

Preparation of the bromine-iodine complex compounds with polyphosphates

Under conditions given in Example II, 2 kg crystalline iodine is mixed with 1.26 kg liquid bromine. Then 16.74 kg oxyethylenized octadecyl alcohol corresponding to the formula $C_{18}H_{37}$-$(OC_2H_4)_{18}$-$OH$ is added and the obtained liquid is mixed with 120.0 kg sodium tripolyphosphate corresponding to the formula $Na_5P_3O_{10}$. To improve the washing properties of the obtained complex compound 8.0 kg sodium dodecylbenzenesulphonate is added and 0.6 kg sodium bromide, as stabilizer.

The product obtained in this manner is diluted with water, for direct use, in a weight proportion from 1:20 to 1:200.

EXAMPLE IV

Preparation of the bromine complex compounds with polyphosphates

In a reactor fitted with stirrer and cooling system 1.8 kg sodium iodide is mixed with 1.4 kg water and at a temperature in the range from 0° to 60° C 1.93 kg liquid bromine is added. The thus prepared aqueous solution of sodium dibromine iodide $NaJBr_2$ is then mixed with 10.9 kg potassium tripolyphosphate corresponding to the formula $K_5P_3O_{10}$ at a temperature not higher than 50° C. To improve the washing properties 1.1 kg sodium dodecylbenzene-sulphonate is added.

The product thus obtained is diluted with water for direct use in a weight proportion from 1:20 to 1:200.

EXAMPLE V

Preparation of the bromine complex compounds with polyphosphates

In a reactor fitted with stirrer and cooling system 1.61 kg lithium iodide is mixed with 1.3 kg water and 1.93 kg liquid bromine is added with continuous stirring at a temperature in the range from 0° to 60° C. The thus prepared aqueous solution of lithium dibromine iodide $LiJBr_2$ is then mixed with 6.8 kg lithium tripolyphosphate corresponding to the formula $Li_5P_3O_{10}$ at a temperature not higher than 50° C.

To improve the washing properties of this product 0.32 kg sulphated lauryl alcohol oxyethylenized with 3 moles of ethylene oxide is added.

The product thus obtained is diluted with water for direct use in a weight proportion from 1:20 to 1:200.

EXAMPLE VI

Preparation of the bromine-iodine complex compounds with polyphosphates

In a reactor fitted with stirrer and cooling system 2 kg crystalline iodine is mixed with 1.26 kg bromine at a temperature of 50°C. The prepared iodine bromide is then mixed with 29 kg oxyethylenized nonylphenol with 8 groups of ethylene oxide containing only small amounts of water, with simultaneous cooling of the reaction mixture, so as to have the temperature of the reaction mixture below 60° C.

The obtained reaction mixture is mixed with 8 kg potassium tripolyphosphate corresponding to the formula $K_5P_3O_{10}$ at a temperature below 50° C, and then 0.81 kg sodium bromide is added, as stabilizer.

The product thus obtained, according to its use, is diluted with water for direct application in a weight proportion from 1:20 to 1:200.

EXAMPLE VII

Preparation of the bromine-iodine complex compounds with polyphosphates

In a reactor fitted with stirrer and cooling system 2 kg crystalline iodine is mixed with 1.26 kg liquid bromine at a temperature below 50° C. The prepared iodine bromide is then mixed with 20.3 kg oxyethylenized monoethanolamides of the tallow fatty acids with 17 groups of ethylene oxide containing only small amounts of water, with simultaneous cooling of the reaction mixture, so as to have the temperature of the reaction mixture below 60° C.

The prepared liquid is mixed with 4.5 kg lithium tripolyphosphate corresponding to the formula $Li_5P_3O_{10}$ at a temperature below 50° C and 0.69 kg lithium bromide is added, as stabilizer.

The product thus obtained, according to its use, is dilulted with water for direct application in a weight proportion from 1:20 to 1:200.

We claim:

1. A process for preparing alkaline polyphosphate complexes of the formula $Me[PO_3ME]_x$-$OH$...$Br$-$Br$...$HO$-$[PO_3Me]_x Me$ wherein Me represents an alkali metal atom, and x is an integer of from 2 to 50, which comprises reacting one mole of a compound selected from a bromoiodate ion, $[IBr_2]^-$ and a bromine-non-ionic surfactant complex with not more than 2 moles of a polyphosphate of the formula $Me[PO_3Me]_x$-OH, wherein Me and x are as defined above, at a temperature range of about 0°–50°C.

2. Method according to claim 1, wherein the dibromoiodate ions, $[IBr_2]^-$, are prepared by reacting liquid bromine with a saturated aqueous solution of alkali iodide in a stoichiometric or nearly stoichiometric proportion at a temperature in the range of 0°–60°C.

3. Method according to claim 1, wherein the bromine-non-ionic surfactant complex compounds are prepared by reacting the dibromoiodate ion, $[IBr_2]^-$, with non-ionic surfactants in a stoichiometric proportion of reactants being not more than 1 mole dibromoiodate ion per 2 moles of surfactant.

4. A process for preparing alkaline polyphosphate complexes of the formula $Me[PO_3Me]_x$-OH...I-Br...HO-$[PO_3Me]_x$Me wherein Me represents an alkali metal atom and x is an integer of from 2 to 50 which comprises reacting not more than one mole of a compound selected from iodine bromide and a bromine-iodine non-ionic surfactant complex with a polyphosphate of the formula $Me[PO_3Me]_x$-OH wherein Me and x are as defined above, at a temperature range of about 0°–50°C.

5. Method according to claim 4, wherein iodine bromide is prepared by reacting bromine with iodine in a stoichiometric proportion or nearly stoichiometric proportion at a temperature in the range of 0°–60°C.

6. Method according to claim 4, wherein the bromine-iodine non-ionic surfactant complex compounds are prepared by reacting iodine bromide with non-ionic surfactants in a stoichiometric proportion of reactants being not more than 1 mole iodine bromide per 2 moles of surfactant.

7. Method according to claim 4, wherein the bromine-iodine-polyphosphate complex compounds are additionally stabilized with bromides of alkali metals or alkali earth metals.

* * * * *